United States Patent
Swanson

(10) Patent No.: US 6,652,529 B2
(45) Date of Patent: Nov. 25, 2003

(54) METHOD AND APPARATUS FOR TREATING SUPRACONDYLAR FRACTURES OF THE FEMUR

(76) Inventor: Todd V. Swanson, 2944 Imperial Purple Ct., Las Vegas, NV (US) 89117

( * ) Notice: Subject to any disclaimer, the term of this patent is extended or adjusted under 35 U.S.C. 154(b) by 4 days.

(21) Appl. No.: 09/954,676

(22) Filed: Sep. 12, 2001

(65) Prior Publication Data

US 2003/0055428 A1 Mar. 20, 2003

(51) Int. Cl.[7] .............................................. A61B 17/56
(52) U.S. Cl. .............................. 606/62; 606/64; 606/67
(58) Field of Search ............................. 606/60, 62, 63, 606/64, 65, 66, 67, 68, 72, 75

(56) References Cited

U.S. PATENT DOCUMENTS

| | | | |
|---|---|---|---|
| 4,103,683 A | | 8/1978 | Neufeld |
| 4,622,959 A | * | 11/1986 | Marcus ........................ 606/64 |
| 4,657,001 A | | 4/1987 | Fixel |
| 4,697,585 A | | 10/1987 | Williams |
| 4,913,137 A | * | 4/1990 | Azer et al. ..................... 606/64 |
| 5,167,663 A | | 12/1992 | Brumfield |
| 5,573,536 A | | 11/1996 | Grosse et al. |
| 5,713,902 A | | 2/1998 | Friedl |
| 5,779,705 A | | 7/1998 | Matthews |
| 5,928,235 A | | 7/1999 | Friedl |
| 6,010,505 A | * | 1/2000 | Asche et al. ................... 606/62 |
| 6,224,601 B1 | * | 5/2001 | Friedl .......................... 606/64 |
| 6,261,290 B1 | | 7/2001 | Friedl |
| 6,319,253 B1 | * | 11/2001 | Ackeret et al. ................ 606/64 |
| 6,409,730 B1 | * | 6/2002 | Green et al. ................... 606/72 |

FOREIGN PATENT DOCUMENTS

| | | |
|---|---|---|
| EP | 321170 | 6/1989 |
| EP | 486483 | 5/1992 |
| EP | 521600 | 1/1993 |

OTHER PUBLICATIONS

Friedl, W., *GN Gliding Nail* pp. 2–27; Mar. 1998.
Mize, Roby D., *Supracondylar and Articular Fractures of the Distal Femur*, Chapter 45, pp. 651–662, 1993.

* cited by examiner

*Primary Examiner*—Pedro Philogene
(74) *Attorney, Agent, or Firm*—Weide & Miller, Ltd

(57) ABSTRACT

Methods and apparatus for treating fractures of the distal femur are disclosed. In one embodiment, the apparatus comprises an intramedullary nail and blade. The intramedullary nail has a passage through a distal end for accepting a locking screw and a blade passage which extends through a proximal end of the intramedullary nail. The blade has a surface which when engaged with the femur resists relative rotation between the blade and femur and is also configured to cooperate with the blade passage to resist rotation of the blade with respect to the intramedullary nail. In accordance with a method, the intramedullary nail is extended into the medullary space of a femur from the distal end. The blade is positioned transversely to the intramedullary nail in a portion of the femur distal of the fracture. The blade is fixed, such as with a locking screw, to prevent axial movement relative to the intramedullary nail. A locking member is extended through the femur and the passage in the distal end of the intramedullary nail to fix the distal end of the intramedullary nail to the femur. In another embodiment of the invention, the apparatus includes two blades for passage through the intramedullary nail, each blade when engaging the passage being freely moveable in the passage, but both blades when engaging the passage resisting rotation thereof with respect to the nail. A blade guide is also disclosed, the blade guide connectable to the nail. When connected, a passage through the blade guide aligns with the passage through the nail for use in a forming a passage in the femur into which the blade(s) are positioned. The guide is designed with a low profile, permitting full extension of the knee while the blade(s) is being inserted.

32 Claims, 7 Drawing Sheets

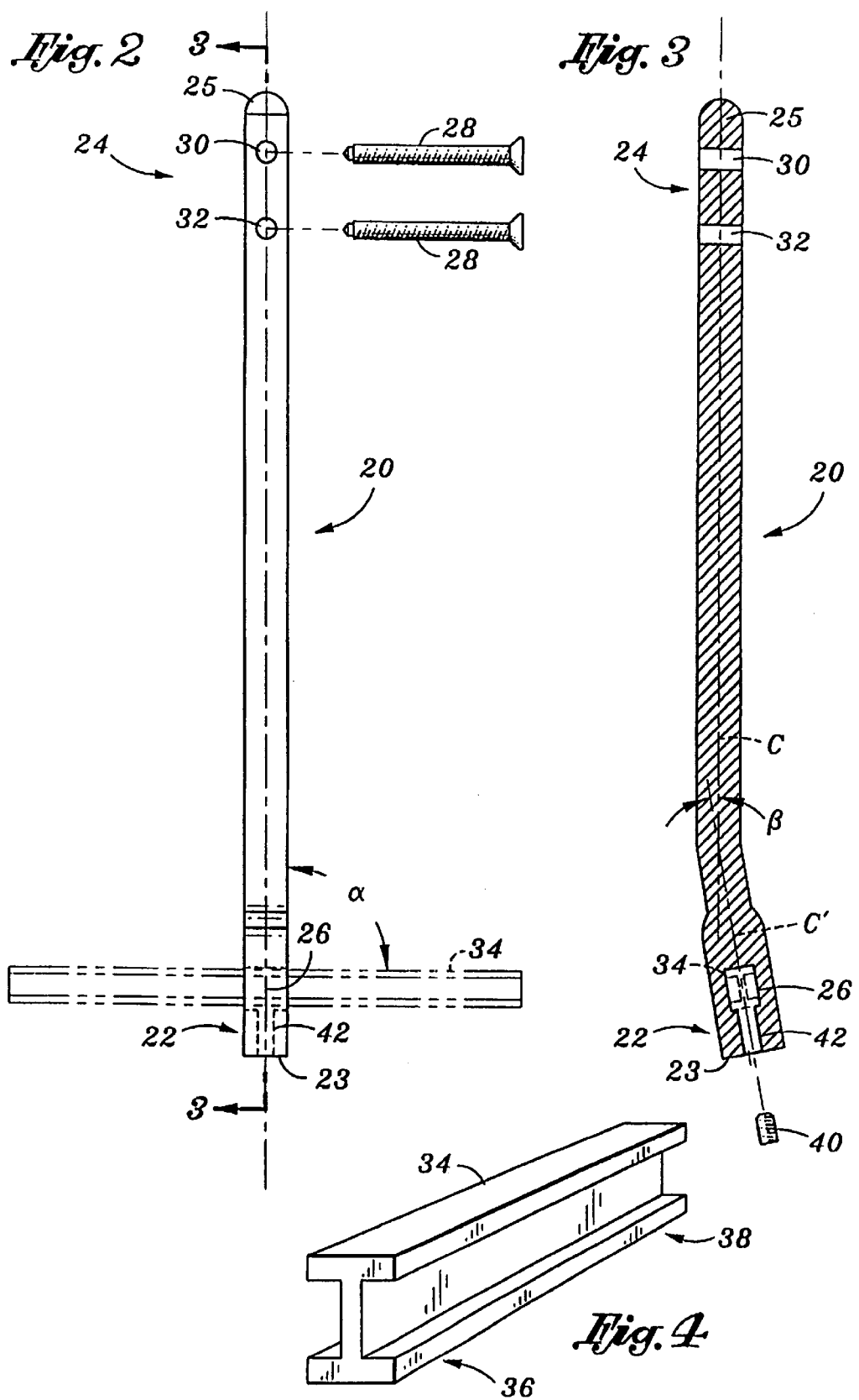

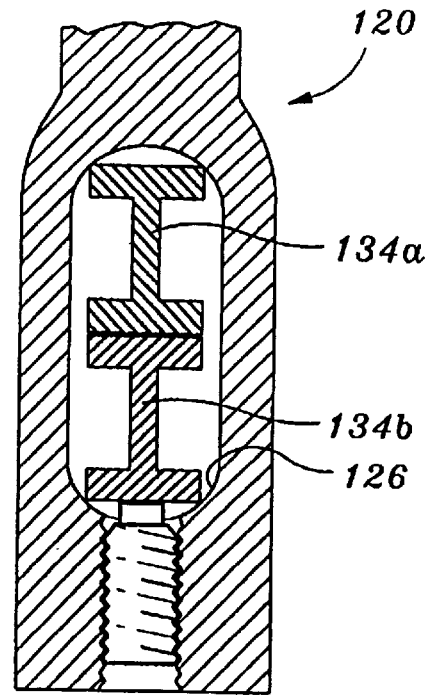
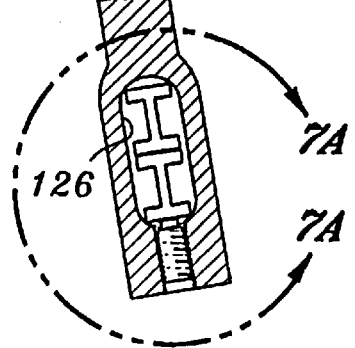
Fig. 7
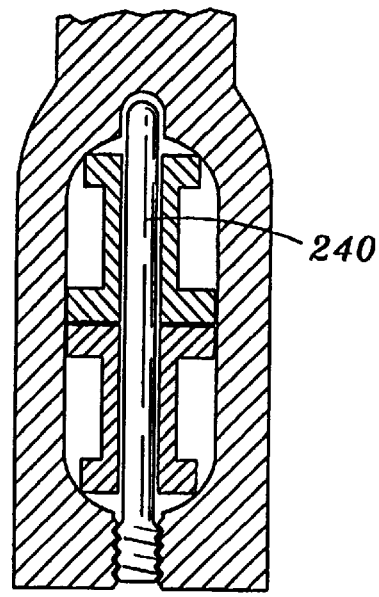
Fig. 7A
Fig. 8

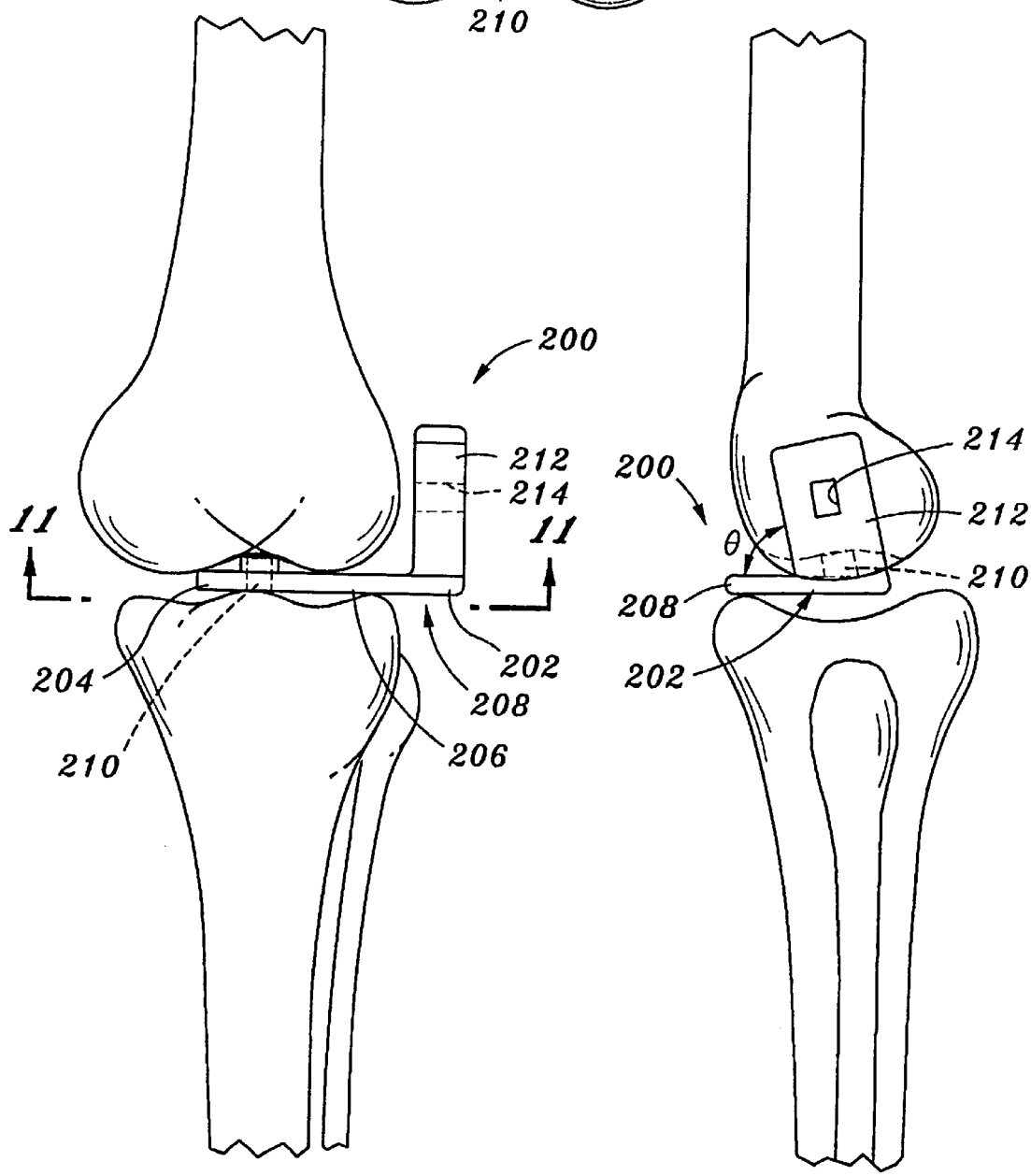

METHOD AND APPARATUS FOR TREATING SUPRACONDYLAR FRACTURES OF THE FEMUR

FIELD OF THE INVENTION

The present invention relates to an apparatus for treating a supracondylar fracture of the femur, and one or more methods of treating such fractures.

BACKGROUND OF THE INVENTION

One injury which may occur in humans is the fracture of the femur. Most commonly, femur fractures are associated with the proximal end of the femur. These types of fractures often result in a fracture of the femoral head from the remaining portion of the femur (known as a "femoral neck fracture") or a fracture between the neck and shaft (known as an "inter-trochanteric fracture").

An injury which occurs less often, but is occurring with increasing frequency, is a fracture of the distal end of the femur. As is known, a pair of condyles are located at the distal end of the femur. Distal femur fractures may be classified into a variety of types with reference to the condyles. In one class, the fracture is between the shaft of the femur and the condyles of the femur (known as a "supracondylar" fracture). In another class of fractures, one or both condyles are fractured from the femur (known as a "condylar" or "intercondylar" fracture). In yet another class of fractures there are multiple fractures, through the supracondylar and intercondylar areas of the femur.

A variety of treatments have evolved for fractures of the distal femur. One common method of treatment is illustrated in FIG. 1A. Illustrated in FIG. 1A is a fracture of the first type, i.e. a fracture of the femur proximal to the condyles with the condyles remaining intact. In accordance with one method of treatment, an exterior plate A is positioned along the exterior of the femur. As illustrated, the plate A has a number of passages there through. Screws B are passed through the plate A into the femur both in the region of the condyles and an area proximal thereto. In accordance with this form of treatment, the plate is used to secure the fractured condyles to the femur.

Other forms of the plate described above are known. For example, the plate may have an angled blade in the form of a "U"-shaped extension (see FIG. 1B), or an outwardly extending screw (see FIG. 1C). This angled blade or screw may be directed into the condyles, and then the other end of the plate affixed to the femur with screws.

The devices illustrated in FIGS. 1A, 1B and 1C (often termed "condylar plates") have a number of disadvantages. One significant problem is that the portion of the femur distal to the fracture, i.e. the portion including the condyles, may rotate with respect to the device. When the condyles are placed in a position of stress, that portion of the femur rotates both with respect to the device and the remainder of the femur. This prevents healing of the fracture or healing in an unnatural or non-anatomically correct position.

A similar problem exists in the arrangement in FIG. 1C in that the entire screw which engages the condyles may rotate relative to the plate. Thus, even if the condyles do not rotate relative to the screw, that portion of the femur may still rotate or move relative to the remainder via rotation of the screw through the plate.

Another problem is that fixation is often made difficult when the femur is osteoporotic. In the example illustrated in FIGS. 1A, 1B and 1C, osteoporotic bone may not permit secure engagement of the screws or blade.

Yet another problem with fixation devices applied to the surface of the femur is that the plate must endure significant cantilever moments that may cause the plate to break or screws to pull out of the bone. These methods therefore require that the leg be immobilized and no weight borne upon the leg until the fracture has healed. For example, with reference to the prior art method and device illustrated in FIGS. 1A, 1B and 1C, the connection of the plate A and the plate itself is generally insufficient to adequately fix the fracture to permit the femur to bear weight. In fact, the plate and screws generally can not tolerate any significant load bearing at all. This again results in stresses which increase healing time or prevent healing, at least without other measures such as external bracing, immobilization or the like.

An improved method and apparatus for treating distal femur fracture is desired.

SUMMARY OF THE INVENTION

The present invention comprises a method of treating a fracture of the distal femur and one or more apparatus for use in a method of treating a fracture of the distal femur.

In one embodiment, the invention comprises an apparatus including an intramedullary nail and a blade. The intramedullary nail is a generally elongate member having a proximal end (nearest to the condyles of the femur) and a distal end. Preferably, the proximal end of the nail is angled at approximately 10 degrees (in the sagittal plane when inserted in the femur) relative to the remainder of the nail to facilitate insertion. One or more locking member accepting passages are provided through the distal end of the intramedullary nail.

A blade passage extends through the proximal end of the intramedullary nail. The blade passage preferably extends through the intramedullary nail at an angle of about 84–96 degrees (i.e. generally perpendicular) to an axis through that portion of the nail.

The blade also has a proximal end and a distal end. At least one of the ends has a shape which is adapted to engage a portion of a femur in a manner resisting rotation of the femur with respect to the blade. In one embodiment, the proximal and distal ends of the blade include at least two generally planar surfaces which intersect at an angle.

In one embodiment, an apparatus is arranged so that the blade may be fixed from moving with respect to the intramedullary nail. Fixation may be rotational and/or axial/translational. In one embodiment, the shape of the blade and the shape of the blade passage are configured so that at least one surface of the blade interacts with at least one surface of the intramedullary nail defining the blade passage to resist or prevent rotation of the blade with respect to the nail. In one embodiment, the blade passage is generally rectangular in shape and the blade is "I" shaped and sized to fit tightly within the blade passage.

In one embodiment, a locking member is provided for locking the blade to the intramedullary nail to resist or prevent axial movement of the blade with respect to the intramedullary nail. In one embodiment, the intramedullary nail includes a passage extending from a proximal tip thereof through the nail to the blade passage. A locking member, such as a screw, may be threaded into the passage into engagement with the blade, locking the blade to the intramedullary nail.

One or more embodiments of the invention comprise a method of treating a fracture of the distal femur. One method includes the step of exposing the distal end of said femur and then extending an intramedullary nail into the medullary space of the femur from the distal end of the femur. Preferably, the intramedullary nail comprises an elongate member having a proximal end and a distal end. The intramedullary nail is extended into the femur until the proximal end of the nail is located near the distal end of the femur. Preferably, the intramedullary nail includes at least one locking member accepting passage located at the distal end thereof.

The method also includes the step of positioning at least one blade member in a portion of the distal end of the femur which is distal to a fracture of the femur. Preferably, the at least one blade member is positioned generally transverse to the intramedullary nail.

The at least one blade member is fixed to the intramedullary nail to generally prevent movement of the at least one blade member with respect to the intramedullary nail. At least one locking member is extended into the femur and the locking member accepting passage located at the distal end of the intramedullary nail.

In one embodiment, the step of fixing the blade to the intramedullary nail comprises mating corresponding portions of the blade and blade passage which are adapted to interfere and generally prevent rotation of the blade with respect to the passage. In another embodiment, the step of fixing includes extending a screw into a passage extending inwardly from the proximal end of the intramedullary nail to the blade passage. The screw is engaged with the blade, fixing the blade from axial and rotational movement with respect to the intramedullary nail.

In another embodiment of the invention, the apparatus includes at least two blades. The blades and passage through the intramedullary nail are shaped and size such that a single blade positioned in the passage may freely move, including rotate, in the passage. However, the passage and blades are configured such that when both blades are positioned in the passage, movement of the blades, including rotation thereof relative to the intramedullary nail, is resisted. In one embodiment, the passage through the intramedullary nail is generally oval in shape, while each blade is "I", "X" or "+" shaped in cross-section.

In accordance with the apparatus and method, an intramedullary nail provides axial support along the length of the femur, including opposing fractured portions thereof. In addition, a blade member provides secure fixation of a fractured portion of the femur relative to the remainder of the femur by engagement with the intramedullary nail. The blade is adapted to engage the fractured portion of the femur and the intramedullary nail in a manner resisting rotation. The blade is also fixed axially with respect to the intramedullary nail. In this manner, movement of the fractured portion of the femur relative to the remainder of the femur in any plane or rotation around any axis is minimized, and healing time is improved.

The apparatus and method of the invention provide a femur fracture treatment which permits use of the leg soon after treatment. The apparatus is configured to withstand high loads and fix the fractured portion of the femur. In the region of the blade passage, the intramedullary nail is preferably enlarged, providing high strength and stiffness.

An additional aspect of the invention comprises a blade guide and a method of using the blade guide to treat a femur fracture using the nail and blade(s) of the invention. In one embodiment, the blade guide has a first, generally planar portion for connection to the proximal end of a nail. The blade guide has a second portion having at least one passage there through. When the blade guide is connected to an intramedullary nail located in the distal end of a femur, the second portion of the blade guide is located at the medial or lateral side of the distal femur. The passage in the second portion of the blade guide aligns with the blade passage through the intramedullary nail.

In use, the blade guide is connected to the proximal end of an intramedullary nail which is then placed, or already placed, in a femur. In one embodiment, the first portion of the blade guide is connected to the nail with a screw. Because of the generally planar, thin nature of the first portion of the blade guide, the knee may be extended after connection of the blade guide.

A passage is then formed in the femur. The passage is formed using the passage through the blade guide which is aligned with the blade passage in the nail. The passage in the femur may be formed by drilling, punching or the like. Thereafter, one or more blades may be placed into the femur and into engagement with the intramedullary nail.

Further objects, features, and advantages of the present invention over the prior art will become apparent from the detailed description of the drawings which follows, when considered with the attached figures.

DESCRIPTION OF THE DRAWINGS

FIG. 2 is a plan view of an intramedullary nail of an apparatus for treating a fracture of the distal femur in accordance with an embodiment of the invention;

FIG. 3 is a cross-sectional view of the intramedullary nail illustrated in FIG. 2 taken along line 3—3 therein;

FIG. 4 is a perspective view of a blade of an apparatus for treating a fracture of the distal femur in accordance with an embodiment of the invention;

FIG. 7 illustrates an apparatus for treating a femur fracture in accordance with another embodiment of the invention, the apparatus including an intramedullary nail and a pair of blades;

FIG. 7A illustrates the pair of blades engaging a passage of the intramedullary nail illustrated in FIG. 7;

FIG. 8 illustrates an apparatus for treating a femur fracture in accordance with another embodiment of the invention, the apparatus including a locking pin;

FIG. 9 is a top plan view illustrating a blade guide in accordance with an embodiment of the invention, the blade guide illustrated attached to an intramedullary nail inserted into a femur;

FIG. 10 is a side view of the blade guide illustrated in FIG. 9;

FIG. 11 is a view of the blade guide in the direction of line 11—11 in FIG. 9;

DETAILED DESCRIPTION OF THE INVENTION

Figure 1A:
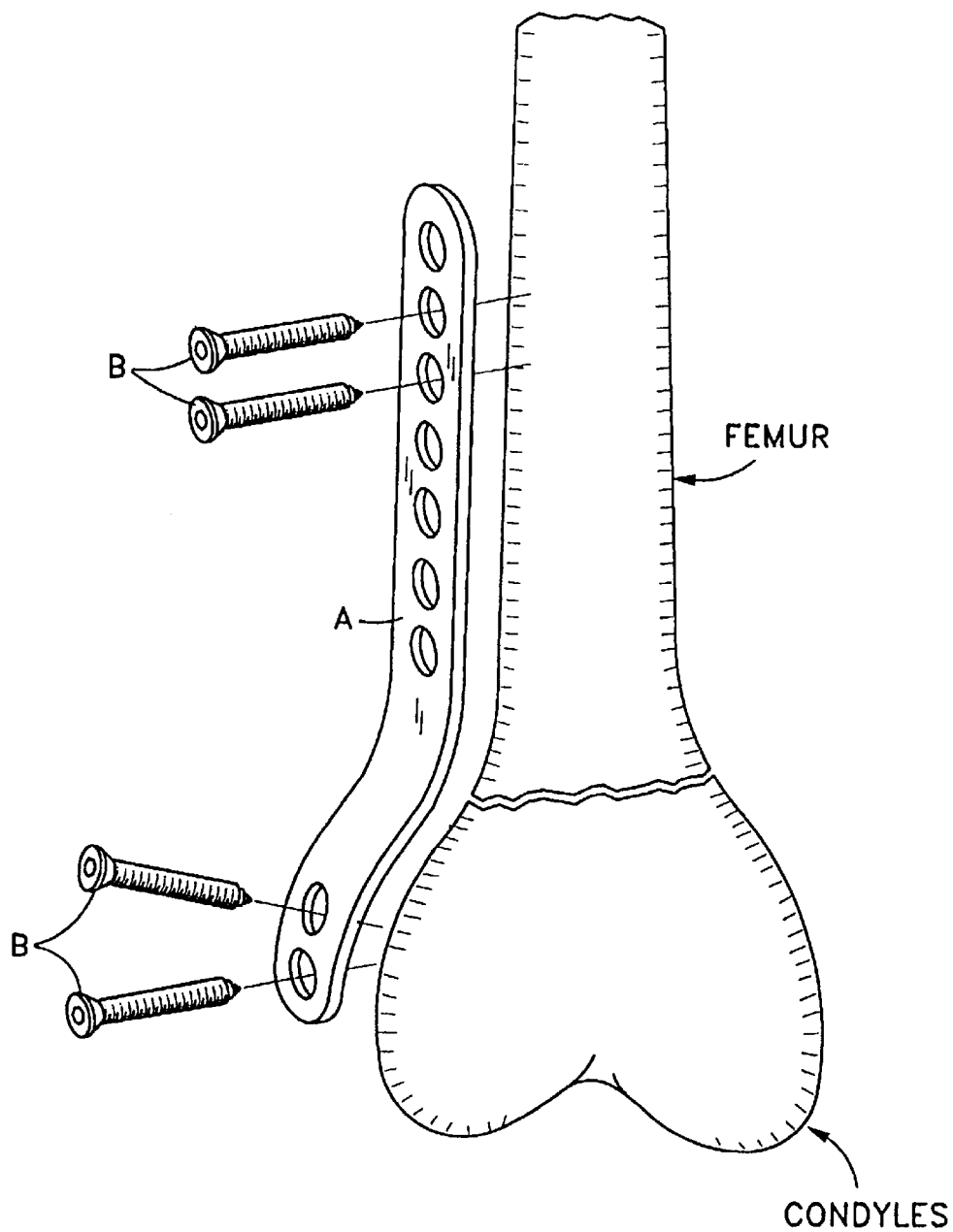
FIG. 1A is a perspective view of a fractured femur and a device for use in immobilizing the fracture in accordance with the prior art.
Figure 1B:
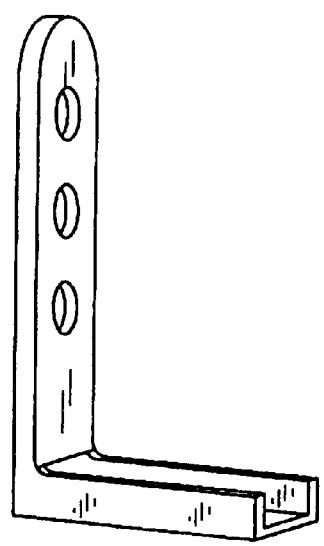
FIGS. 1B and 1C illustrate other devices in accordance with the prior art.
Figure 1C:
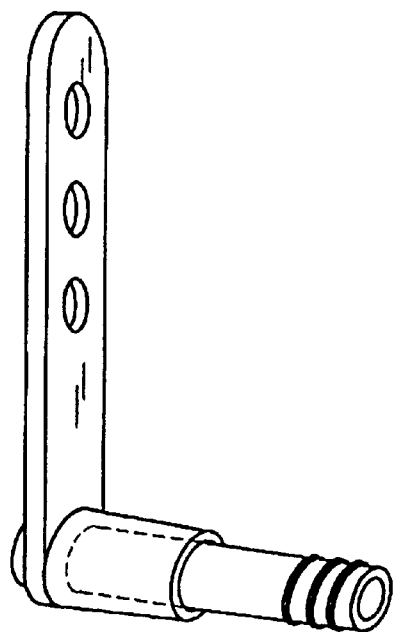

The invention is a method and apparatus for treating fractures of the distal femur. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One or more embodiments of the invention comprise an apparatus for treating a supracondylar femur fracture, otherwise known as a fracture of the distal femur. In general, the apparatus comprises an intramedullary nail for location at least partially in the femur. The apparatus includes at least one stabilizing member for engaging a portion of the femur and the intramedullary nail. The at least one stabilizing member is adapted to cooperate with the intramedullary nail to fix fractured portions of the femur to one another. In one embodiment, the at least one stabilizing member comprises a blade which engages a portion of the intramedullary nail in a secure manner preventing axial and radial movement with respect thereto. The blade is also adapted to engage a portion of the femur in a secure manner, preferably preventing at least rotation relative thereto.

One or more embodiments of the invention comprise a method of treating a fracture of the distal femur. In one embodiment the method comprises a method of placing the intramedullary nail in the femur, and placing the blade in the femur and securing it to the intramedullary nail.

One embodiment of an apparatus for treating a fracture of the distal femur in accordance with the invention will now be described with reference to FIGS. 2–6. As illustrated, an apparatus in accordance with the invention includes an intramedullary nail 20. The nail 20 is referred to as an intramedullary nail because, as described below, at least a portion of the nail 20 is adapted to be located within the medullary space of a femur.

In one embodiment, as illustrated in FIGS. 2 and 3, the intramedullary nail 20 comprises a rod-like member having a proximal end 22 and a distal end 24. As illustrated, the term "end" as used herein is not limited to a terminus of the member, but more generally a region thereof.

Referring to FIG. 3, in one embodiment the intramedullary nail 20 has a generally circular cross-section along most of its length. At the terminus of the distal end 24, the nail 20 preferably forms a generally hemi-spherical or bullet-shaped, smooth distal tip 25. The distal tip 25 of the distal end 24 of the intramedullary nail 20 may have other shapes, but preferably is adapted to be inserted into the femur in a manner reducing the damage to the femur.

In a preferred embodiment of the invention, the intramedullary nail 20 includes a blade passage 26 for accepting a stabilizing member in the form of a blade there through. Details of such a blade are provided below. As illustrated, the blade passage 26 is located at, and extends through, the proximal end 22 of the intramedullary nail 20. Preferably, a portion of the intramedullary nail 20 about a blade passage 26 is of an increased dimension. In one embodiment, the dimension of the nail 20 is increased in a first plane there through, and not in a second plane extending generally perpendicular to the first. In a preferred arrangement, the increased dimension is in a plane which corresponds to the sagittal plane when the nail 20 is positioned in a femur, while the nail 20 retains the same dimension in the coronal plane.

In a preferred embodiment, a substantial portion of the intramedullary nail 20 is generally straight, extending along a central axis. In a preferred embodiment, however, the nail 20 bends at an angle distal of the area of increased dimension. In one embodiment, the nail 20 bends at approximately a 10 degree angle from the central axis C, extending along an offset axis C'. As described below, the exact bend angle and location of the bend is preferably selected to aid in insertion of the nail 20 into the femur and align the nail 20 centrally along the femur.

The proximal end 22 of the intramedullary nail 20 preferably terminates in a proximal tip 23. In one embodiment, the proximal tip 23 is generally planar, the plane defined by the tip positioned generally perpendicular to the axis. Preferably, the blade passage 26 is located some distance along the axis towards the distal end 24 of the intramedullary nail 20 from the proximal tip 23.

If the intramedullary nail 20 is constructed with a great length, the intramedullary nail 20 may be bent or bowed slightly to accommodate the curvature of the femur. It is noted that when the blade passage 26 is generally perpendicular to the portion of the intramedullary nail 20 through which it passes, then the intramedullary nail 20 may be used in either the right or left femur even though it is provided with a bend.

The size and dimensions of the intramedullary nail 20 may vary. In general, the intramedullary nail 20 is sized to fit within the medullary space of a femur, extending from a distal end of the femur towards the proximal end thereof. In one embodiment the intramedullary nail 20 is approximately 250–360 mm long from end to end. The intramedullary nail 20 has a diameter of about 10–16 mm in the area excepting the enlarged portion of the proximal end 22. The intramedullary nail 20 has a diameter of about 12–20 mm in the enlarged area thereof about the blade passage 26. The outer surface of the intramedullary nail 20 is preferably polished smooth and burr-free. In order to provide for a maximum load carrying capability relative to the size of the intramedullary nail 20, the intramedullary nail 20 is preferably of a substantially solid (i.e. not substantially hollow) material construction.

In one embodiment, a narrow passage may be provided through the intramedullary nail 20 from the proximal tip 23 to the distal tip 25. In this arrangement, the intramedullary nail 20 has a cannula type arrangement permitting it to be passed along a guide wire for insertion into a femur.

In one embodiment, means are provided for securing the distal end 24 of the intramedullary nail 20 to a portion of a femur in which it is inserted. In a preferred embodiment, the means includes at least one locking member. The locking members may comprise pins or screws 28. Such screws 28 are well known. The screws 28 are adapted to pass through passages 30,32 in the intramedullary nail 20. In one or more embodiments, the passages 30,32 are preferably spaced about 20–40 mm apart. Instead of screws, bolts having self-cutting threads may be used. One or more of the passages 30,32 maybe oval or elongate in shape to allow axial sliding of the nail in the femur for compression at the fracture site. Further, the passages 30,32 may be located in the sagittal or coronal plane.

The screws 28 may have a variety of sizes. In one embodiment, each screw 28 is about 30–35 mm long and about 4–6 mm in outer diameter.

As detailed above, in a preferred embodiment, at least one member is adapted to connect to the intramedullary nail 20 and engage the femur in a secure manner. In one embodiment, this member comprises a blade 34.

An embodiment of a blade 34 in accordance with the invention will be described with reference to FIG. 4. In a preferred embodiment, the blade 34 is arranged to engage a portion of a femur in a manner which generally prevents movement of the engaged portion of the femur relative to the blade 34. In one embodiment, the blade 34 is a generally elongate member having a proximal end 36 and a distal end 38. As in the case of the intramedullary nail 20, reference to an "end" is not limited to the terminus of the blade 34, but generally includes a portion of the blade 34.

In one or more embodiments, at least a portion of either or both the proximal end 36 and distal end 38 of the blade 34 has a shape designed to engage a portion of a femur and resist relative rotation of the femur with respect to the blade 34. In a preferred embodiment, that portion of the blade 34 has a cross-section which is not circular or generally circular, which does not form a helix/spiral, and which includes at least two or more generally planar surfaces which meet at an angle. Preferably, the angle at which the planar surfaces intersect is an acute or perpendicular angle between 20 and 90 degrees. In one embodiment, the portion of the blade 34 at which the surfaces intersect is at a maximum radial distance from the center of the blade 34, so that the intersection engages the femur when placed in a generally circular bone.

One specific embodiment of the blade 34 embodying these characteristics is illustrated in FIG. 4. This blade 34 has a generally "I" shaped cross-section along its length. Other cross-sectional shapes may be provided, such as "+" "X" and "T".

The dimensions of the blade 34 may vary. In one or more embodiments, the blade 34 is about 40–60 mm long. The blade 34 has width and depth dimensions which permit it to fit within an appropriately sized and shaped blade passage.

As described in more detail below, the blade 34 is adapted to engage the intramedullary nail 20. As noted above, the intramedullary nail 20 includes a blade passage 26 for acceptance of at least a portion of the blade 34 there through.

In the embodiment where the blade 34 has a generally "I" shaped cross-section, the blade passage 26 may be generally rectangular in shape, as illustrated in FIGS. 2 through 6. In one or more embodiments, as best illustrated in FIGS. 2 and 4, the blade passage 26 extends through the intramedullary nail 20 at an angle α. In one embodiment, the angle α is between about 84 and 96 degrees, and more preferably 90 degrees, with respect to the axis C'. In other words, the blade passage 26 extends through the intramedullary nail 20 generally perpendicular (i.e. 84–96 degrees offset) to a direction along the length of the nail. It is possible for the blade passage 26 to extend through the nail 20 at greater or lesser angles.

In a preferred embodiment, the blade passage 26 through the intramedullary nail 20 is adapted to cooperate with the blade 34 in order to limit, if not generally prevent, movement of the blade 34 with respect thereto at one or more times.

In one embodiment, means are provided for preventing both rotational and axial movement of the blade 34 relative to the intramedullary nail 20. As illustrated, the means for preventing rotational movement may comprise a configuration of the blade 34 and blade passage 26 relative to one another. The size and shape of the blade 34 is selected with reference to the size and shape of the blade passage 26, such that one or more surfaces of the blade 34 and blade passage 26 engage one another when an attempt is made to rotate the blade 34 relative to the blade passage 26, preventing or limiting relative rotation thereof.

In one or more embodiments, the means for preventing axial movement comprises at least one locking member. Referring to FIG. 3, the locking member may comprise at least one screw 40. As illustrated, the intramedullary nail 20 includes a passage 42 extending from the proximal tip 23 to the blade passage 26. The passage 42 is threaded. Preferably, the passage 42 extends generally parallel to, if not along, the axis C' extending through that portion of the nail 20.

The screw 40 is adapted to be inserted into the passage 42. The screw 40 has external threads thereon for engaging the threaded passage 42.

A method of treating a fracture of the distal femur will now be described primarily with reference to FIGS. 5 and 6. In this description, reference will be made to the apparatus illustrated in FIGS. 2–4 and described in detail above.

The distal end of the femur is exposed. This may be accomplished with a variety of surgical techniques and generally occurs with the knee flexed or bent.

A bore is created in the femur. Preferably, the bore extends from the distal end of the femur, including the portion distal of the fracture of the femur (such as the condyles), through the interior of the femur towards its proximal end. The length of the bore is preferably selected so that all or substantially all of the intramedullary nail 20 may be located within the bore. In general, it is undesirable for the proximal end 22 of the intramedullary nail 20 to extend outwardly from the femur at its distal end once the nail 20 is placed. The intramedullary nail 20 is placed in the bone. As stated above, a guide wire may be placed in the bone and then the nail 20 passed thereover for guiding the nail 20 into the bone.

The blade 34 is placed into engagement with both the femur and the intramedullary nail 20. In one embodiment, a passage or bore is formed through the fractured portion(s) of the femur. In a preferred embodiment, the shape of the passage or bore which is created is the same as the cross-sectional shape (or perimeter profile) of the blade or blades which are to be positioned therein. For example, referring to FIG. 5 where the fracture is a fracture proximal to the condyles, the bore or passage is formed through the condyles. The bore extends inwardly from an exterior surface of the femur. The bore preferably aligns with the blade passage 26 through the intramedullary nail 20. Preferably, the bore and the blade passage 26 are co-axial, with little or no angular offset there between. A large angular offset will prevent extension of the blade 34 through the bore and blade passage 26.

The blade 34 is inserted into the bore. The blade 34 is pressed inwardly until it passes through the blade passage 26. During insertion of the blade 34, the blade 34 is oriented so that it aligns with the passage 26. For example, referring to FIG. 5, the blade is oriented so that its larger height dimension aligns with the larger height dimension of the rectangular blade passage 26.

The blade 34 is fully extended into the bore or passage, preferably until the blade 34 does not protrude significantly from the exterior of the femur. Once the blade 34 is positioned, it is locked to the intramedullary nail 20. In one embodiment, the screw 40 is threaded into the passage 42 extending into the proximal end 22 of the nail 20. The screw 40 is threaded inwardly until it engages the blade 34. So engaged, the screw 40 applies pressure to the blade 34, binding it against the intramedullary nail 20 within the blade passage 26.

One or more screws 28 are passed from an exterior portion of the femur into the femur and through a corresponding passage 30,32. In one embodiment, two screws 28 are passed through corresponding passages 30,32 in the intramedullary nail 20. Locator bores may be formed in the femur before engaging the screws 28 with the femur, thus ensuring that the screws engage the passages 30,32 in the nail 20. Preferably, the screws 28 are extended into the femur until a head of the screw is generally flush with the exterior of the femur. In addition, the screws 28 are preferably of a length that when fully engaged, a portion of each screw engages the femur on either side of the intramedullary nail 20.

Various configurations of apparatus other than that illustrated in FIGS. 2–4 and detailed above are contemplated as within the scope of the invention.

With respect to the fixation of the distal end of the nail 20 to the femur, in one or more embodiments there may be provided as few as one or more than two screws 28 or other means for attaching or securing the intramedullary nail 20 to the femur. For example, three passages may be provided through the intramedullary nail 20 for accepting three screws for securing the intramedullary nail to the femur. In one or more embodiments, the holes for accepting the one or more screws 28 can be in coronal, sagittal, or a combination of such planes with respect to the femur and intramedullary nail.

In one or more embodiments, additional means may be used to connect the nail 20 to the femur. For example, as illustrated in FIG. 6 the intramedullary nail 20 may be provided with one or more additional passages or bores 44 for accepting screws or other locking members.

The cross-section of the intramedullary nail 20 may be other than circular. For example, in one embodiment the cross-section of the intramedullary nail 20 may be oval in one or more areas. In one embodiment, the cross-section of the intramedullary nail 20 may be circular except in the enlarged area about the blade passage 26, wherein the cross-section is generally oval.

The means for securing the blade 34 to the intramedullary nail 20 may be other than that described above. For example, more than one screw may be use to secure the blade 34 to the intramedullary nail 20 to prevent axial movement thereof. Other means may be provided for securing the blade 34 to the intramedullary nail 20. For example, the means may comprise a pin which may engage the intramedullary nail in a locked and an unlocked position (such as by rotation where a catch on the pin engages a portion of the nail). In one embodiment, a pin or similar member may be arranged to extend into the intramedullary nail and also all or a portion of the blade. In this arrangement, the blade may be provided with closely spaced indentations or passages or an oblong passage which may be aligned with the passage 42 in the intramedullary nail.

The blade 34 may be configured other than as illustrated. In one embodiment, only the proximal and distal ends 36,38 of the blade 34, or portions thereof, are configured to resist rotation when located in the femur. A portion between the ends 36, 38 of the blade 34 may have a configuration which varies from the ends. For example, a portion of the blade 34 between its ends 36,38 which is positioned within the blade passage 26 when the blade 34 is engaged with the nail 20 may have a circular or other cross-section. In that event, rotation and axial movement of the blade 34 with respect to the nail 20 may be prevented with the screw alone.

The blade 34 may have a variety of configurations other than specifically described above. As noted, it is desired that the blade 34 have one or more generally planar outer surfaces which meet at an angle. Other than the shapes described above, the blade may have a star, square or triangular shaped perimeter. Of course, a wide variety of other configurations may be provided.

The various components of the apparatus of the invention may be constructed from a wide variety of materials. In a preferred embodiment, the material is selected to provide appropriate strength and stiffness, and be bio-compatible with a human, including a human's immune system. Preferably, the material is biologically inert and sterilizeable. One preferred material is stainless steel. Titanium, cobalt, chromium and other materials may be used.

FIGS. 7, 7A and 8 illustrate another embodiment of an apparatus for treating a fracture of the distal femur. This embodiment apparatus includes an intramedullary nail 120 and a first blade 134a and a second blade 134b.

In general, the intramedullary nail 120 is similar to the intramedullary nail 20 described above and illustrated in FIGS. 2 and 3. In this embodiment, however, the intramedullary nail 120 includes a passage 126 which is generally oval in shape. The first and second blades 134a, b are also configured similar to the blade 34 described above and illustrated in FIG. 4.

In this embodiment of the invention, the blade passage 126 and blades 134a, b are configured to cooperate so that the blades 134a, b securely engage the intramedullary nail 120 to prevent relative movement there between. Preferably, the relative movement which is resisted or prevented is relative rotational movement of either or both blades 134a, b with respect to the intramedullary nail 120.

In a preferred embodiment, the size of the passage 126 and the size of each blade 134a, b is selected so that when a single blade 134a, b is located in the passage 126, that blade 134a, b is freely moveable, including rotatable. However, the sizes of the blades 134a, b and passage 126 are selected so that when the second blade 134a, b is positioned in the passage 126 along with the first blade 134a, b, rotation of the blades 134a, b with respect to the intramedullary nail 120 is resisted.

In one embodiment, the oval has a pair of foci which are located fairly proximate to one another. The blades 134a, b have a width which is nearly as great if not greater than their height. In one embodiment, the total height of the two blades 134a, b stacked upon one another is approximately the same as the height of the blade 34 illustrated in FIG. 4, such that the size of the passage in the nail 120 in which the blades 134a, b are placed is not so great that the strength of the nail is compromised.

Use of this embodiment apparatus is similar to that described above. One of the blades 134a, b is extended through the passage 126. The second blade 134a, b is also extended through the passage 134a, b. A screw or similar member is preferably again extended into the intramedullary nail 120 for engaging one of the blades 134a, b, generating a force which further locks the blades 134, a, b in place and preventing rotational and axial movement thereof.

An advantage of this embodiment apparatus is a secure locking structure and use of smaller blades, each of which alone is easier to manipulate. The arrangement of the blades 134a, b and passage 126 is such that the first blade 134a, b inserted into the passage 126 may be inserted in any orientation and is freely moveable. The second blade 134a, b is then inserted in a specific orientation to mate with the blade which was first inserted, thus securing the blades 134a, b. In addition, insertion of the first blade aids in stabilizing the position of the fracture. Then, after insertion of the first blade, further alignment of the fracture is possible before locking the position of the fracture by insertion of the second blade.

In similar fashion to that described above, the intramedullary nail 120 and the blades 134a, b may have a wide variety of configurations. For example, a number of configurations of two or more blades may be provided which cooperate with a passage as described above to achieve a locking effect. In one embodiment, the blades may have an "X" "+" "T" or other cross-section or a combination of these cross-sections, where the legs of the blades abut to achieve the locking. Also, the shape of the passage may vary. As noted, it is preferred that the shape and size of the passage and blades be chosen such that individual blades positioned in the passage are moveable (including rotatable), but whereby locking is achieved when the second, third or other additional blade is located in the passage. For example, in one embodiment, the portion of each blade which extends through the passage may be circular. Each blade may include a cut-out, such that when the cut-outs are aligned, a bar may be extended along the length of the blades in the aligned cut-outs, locking the blades together.

In one variation of the invention, movement of the blade or blades may be substantially limited by a locking pin. Referring to FIG. 8, a passage may be provided through the blade or blades, which passage(s) may be aligned with the passage at the proximal end of the nail. Instead of providing a set screw, an elongate pin may be extended through the passage in the nail and the passage in each blade. In a preferred embodiment, a locking passage extends through the nail at an opposing portion of the blade passage opposite the passage extending from the proximal end of the nail. The tip of the pin is extended into this opposing passage, preventing movement of the pin and the blade through which it extends. Again, the pin is preferably locked in position with threads located thereon which engage threads in the passage at the proximal end of the nail.

Regardless of the shape of the portion of the blade(s) which engage the passage 126, it is desired that at least a portion of the remainder of the blades 134a, b be arranged to resist rotation of the femur with respect to the blade(s).

In accordance with the present invention there is also provided a blade guide 200. The blade guide 200 of the invention, including its use, will be described with reference to FIGS. 9–13.

As illustrated in FIGS. 9–11, the blade guide 200 has a generally planar mounting portion 202. Referring to FIG. 11, the mounting portion 202 is generally "C" or "U"-shaped. In one embodiment, the mounting portion 202 of the blade guide 200 includes a nail attachment portion 204, an extension 206, and a guide attachment portion 208. The nail attachment portion 204 and guide attachment portion 208 extend generally parallel to one another, and are connected by the extension 206 extending there between.

A passage 210 is provided through the nail attachment portion 204, preferably near an end thereof opposite the extension 206. As detailed below, the passage 210 is adapted to permit attachment of an intramedullary nail 20 of the invention to the blade guide 200.

The nail attachment portion 204 has a length sufficient to extend from a centerline of a femur to a point exterior to the femur, as best illustrated in FIG. 11. The extension 206 extends from the nail attachment portion 204 generally perpendicular to the nail attachment portion 204. The extension 206 has sufficient length to extend outwardly of the femur in a direction perpendicular to the nail attachment portion 204 (i.e. to a medial or lateral portion thereof), as also illustrated in FIG. 11.

The guide attachment portion 208 extends perpendicular to the extension 206, preferably in a direction back towards a femur (i.e. in the same direction from the extension 206 as the nail attachment portion 204).

As best illustrated in FIGS. 9 and 10, a guide 212 extends from the guide attachment portion 208. The guide 212 preferably extends upwardly from the guide attachment portion 208 generally perpendicular to a plane in which the mounting portion 202 of the blade guide 200 is positioned.

As illustrated, the guide 212 is a generally rectangular body. As illustrated, the guide 212 extends upwardly from the guide attachment portion 208 at an angle $\theta$. This angle $\theta$ is preferably less than 90 degrees, and more preferably between 60 and 85 degrees. The exact angle is chosen so that a blade passage 214 is aligned with the blade passage 26 in an intramedullary nail 20 located in the femur, as detailed below.

The blade passage 214 is provided through the guide 212 in a plane parallel to the mounting portion 202 of the blade guide 200. The blade passage 214 is sized to permit passage of a blade of the invention there through under close tolerances. Of course, in an embodiment where the passage 26 through the intramedullary nail 20 is at an angle other than perpendicular thereto (such as 84 degrees) then the blade passage 214 is similarly offset and not parallel to the mounting portion 202 (i.e. offset by 6 degrees in that case).

In general, the blade guide 200 of the invention is designed to aid in the formation of a blade passage into or through a femur and location of a blade in the passage or bone formed in the femur. More particularly, the blade guide 200 is designed for use in forming a blade passage through a femur in alignment with a blade passage through an intramedullary nail of the invention, and location of a blade or blades in that passage and the nail.

Figures 12, 13:
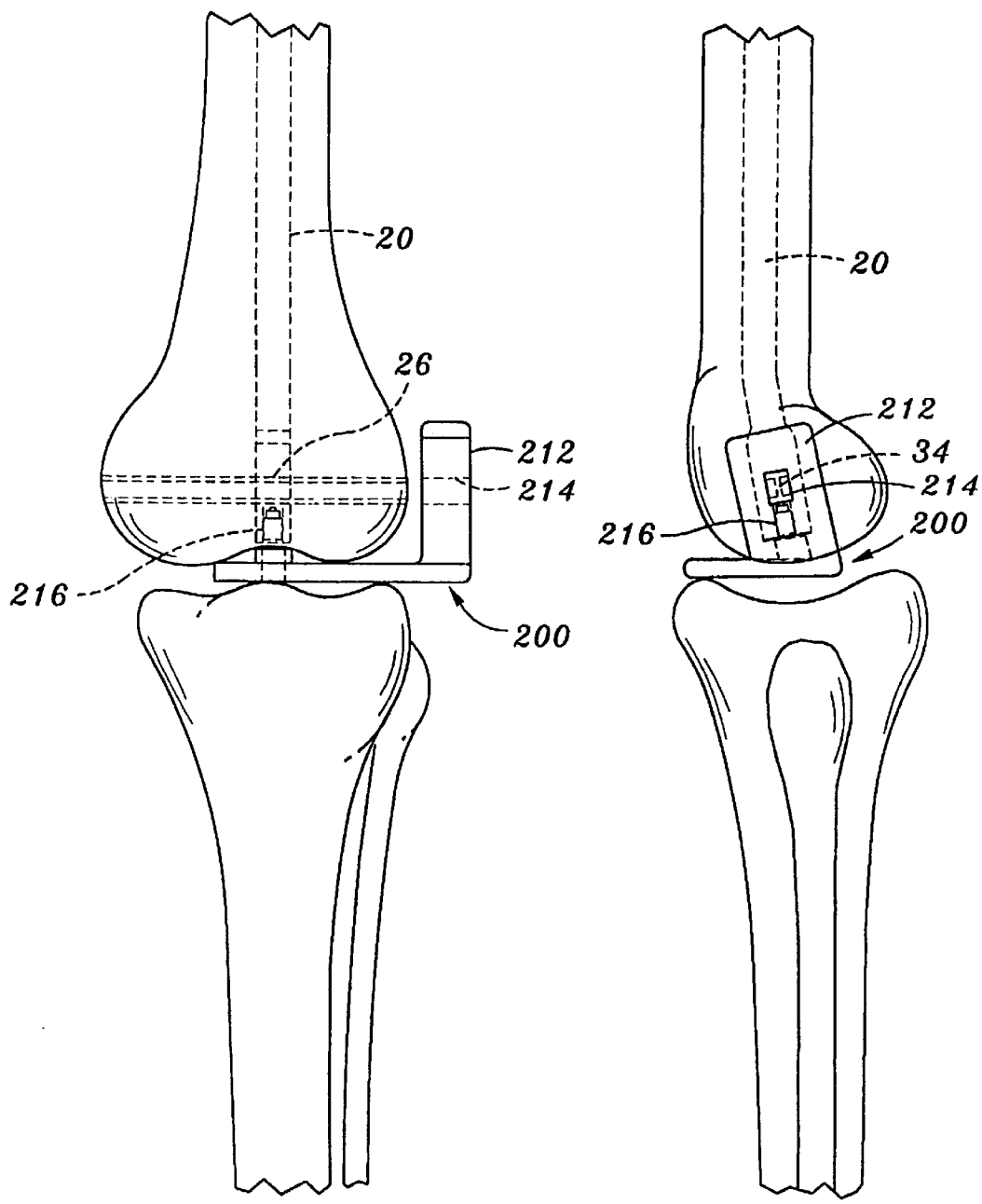
FIG. 12 is a top plan view illustrating the correspondence between the blade guide of the invention and a blade inserted into a femur.
FIG. 13 is a side view of the blade guide and inserted blade illustrated in FIG. 12.

Use of the blade guide 200 of the invention will be described with reference to FIGS. 12 and 13. In a preferred embodiment of the invention, an intramedullary nail in accordance with the invention is placed in a femur, such as in a manner described above. Reference is specifically made to the embodiment nail 20 illustrated in FIGS. 2–6, though other devices may be used. As detailed above, and as illustrated in FIGS. 12 and 13, the nail 20 has a blade passage 26 extending there through.

The blade guide 200 of the invention may be attached either before insertion of the nail 20 or after insertion, preferably at the proximal end 22 of the nail. In one embodiment, the blade guide 200 is attached to the intramedullary nail 20 with a screw or bolt 216. The screw or bolt 216 is adapted to pass through the passage 210 in the nail mounting portion 206 of the blade guide 200, engaging the blade guide 200 and then the nail 20. As described above, in one embodiment, such as that illustrated in FIGS. 3 and 7, the nail 20 includes a passage extending inwardly from the proximal end 22 thereof, that passage being threaded. In one embodiment, the screw or bolt 216 may comprise the screw 40 which is ultimately used to affix the blade to the nail 20, as illustrated in FIG. 6, or may alternatively comprise a different, similarly threaded screw or bolt. In such an arrangement, the screw is first not threaded into the blade passage 26, but only into engagement with the blade guide 200 and nail 20.

As detailed above, when the nail 20 is inserted into the femur, such is preferably done with the knee flexed or bent to permit access to the axis of the femur. After the blade guide 200 is affixed to the intramedullary nail 20, however, the knee may be extended, as illustrated in FIGS. 12 and 13. At this time, the blade guide 200 is affixed to the intramedullary nail 20 and extends from the femur with the guide 212 at a location exterior to the femur. Furthermore, the passage 214 in the guide 212 of the blade guide 200 is aligned with the blade passage 26 through the intramedullary nail 20, when considering both location and orientation.

In a next step, a passage is formed through the femur into which a blade 34 or blades of the invention may be located. In one embodiment, small pilot holes may be drilled through the femur by locating a drill bit at each corner of the passage 214 in the guide 212, and then drilling inwardly through the femur. A punch may then be used to knock out the portion of the femur bounded by the pilot holes.

Of course, a wide variety of techniques may be used to form the blade passage through the femur. Such techniques may include drilling, punching, boring or the like. In one or more embodiments, one or more additional templates may be connected to the blade guide 200 if a particular portion of an area aligned with the passage 214 is to be drilled or bored. Such templates are useful in aligning and stabilizing a drill bit or other member used to drill a portion of a femur aligned with the portion of the passage 214. In one embodiment, one or more templates or the like may be placed into engagement with the passage 214, each template having one or more smaller passages defined there through for accepting a drill bit or the like. Such templates are useful in particularly locating a bit or the like for forming a passage. Preferably, the template is removable, so that once the passage in the femur is formed, the blade may be passed through the passage in the blade guide into engagement with the femur.

It will be appreciated that because the passage 214 through the guide 212 is aligned with the blade passage 26 through the intramedullary nail 20, the blade passage formed by drilling, punching or the like is aligned through the femur with the blade passage 26 in the nail 20.

Once the blade passage is formed through the femur, the one or more blades 34 of the invention may be located therein. The blade or blades 34 are passed through the passage 214 in the guide 212 portion of the blade guide 200. Once positioned in the femur and the blade passage 26 through the intramedullary nail 20, the blade(s) 34 may be affixed to the nail 20 in a manner described above. For example, the screw 40 (which may also comprise the screw 216) may be threaded inwardly into engagement with the blade(s) 34, locking it (them) in position.

After placement of the blade(s) 34, the blade guide 200 may be removed from the nail 20.

It will be appreciated that the exact configuration of the blade guide 200 depends substantially upon the configuration of the intramedullary nail to ensure alignment of the passages to be formed. For example, as the angle of the bend in the intramedullary nail 20 (angle β as illustrated in FIG. 3) varies, so must the angle of the guide 212 portion of the blade guide 200 and/or the location of the passage 214 therein.

Figures 5, 6:
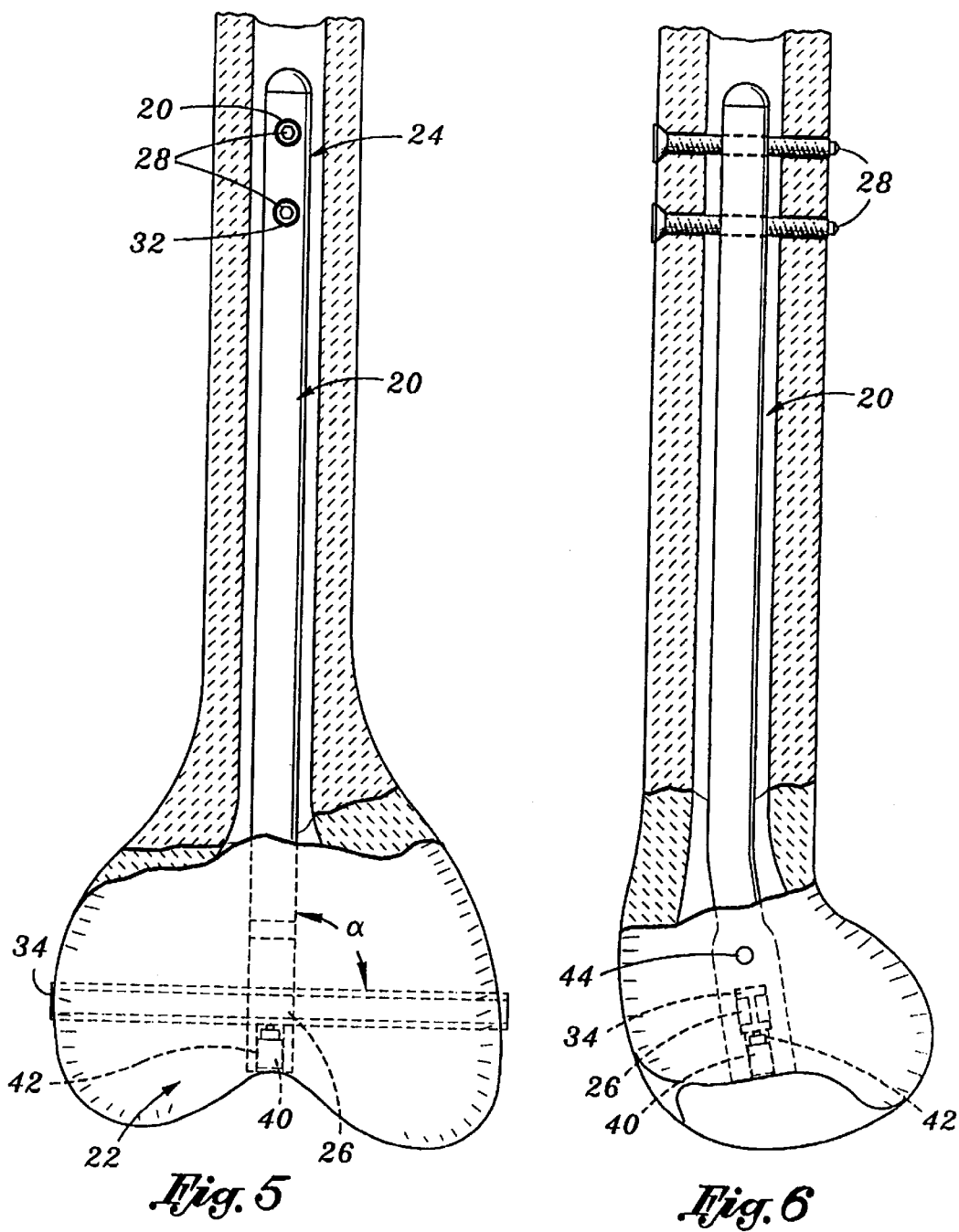
FIG. 5 illustrates in partial cross-sectional view an intramedullary nail and connected blade inserted into a fractured distal femur.
FIG. 6 illustrates the assembly of FIG. 6 rotated ninety-degrees.

In an embodiment where the blade passage 26 through the intramedullary nail 20 is tilted (such as at an angle α as illustrated in FIG. 5), then the passage 214 through the guide 212 portion of the blade guide 200 is similarly oriented.

The exact shape and size of the passage 214 is preferably dependent upon the shape and size of the blade or blades which are to be placed. Thus, the size and shape of the passage 214 may be dictated in a similar manner to the passage 26 described above with respect to the intramedullary nail 20.

Preferably, the blade guide 200 is made of a similar material as the nail 20, such as an inert, sterilizeable material. At least the portion of the blade guide 200 surrounding the passage 214 is preferably constructed of a very durable material so as to prevent damage thereto when drilling or punching.

In one embodiment, the blade guide 200 is constructed as a single or unitary element. In one or more embodiments, the blade guide 200 may comprise multiple elements which are connectable. In one embodiment, the relative location and/or orientation of the portions of the blade guide 200 may be adjustable. In this manner, the blade guide 200 may be adapted for use in a variety of different situations, such as to accommodate differing sizes and shapes of femurs. In one embodiment, the guide 212 portion of the blade guide 200 may be removable, and more than one guide 212 may be provided. One guide 212 may have a plurality of passages there through or a collet or the like for aligning drill bits. Another guide 212 may then have a blade aligning passage for insertion of the blade(s) into the femur.

It will be appreciated that the exact order of the steps of the method(s) described herein may vary. For example, it is possible to use the blade guide 200 to form the passage in the femur and then remove the blade guide 200 before placing the blade(s).

As stated, the first or mounting portion 202 of the blade guide 200 is preferably generally planar and relatively thin. This construction allows the knee to be extended even when the blade guide 200 is connected to the intramedullary nail 20. This is important, for when the knee is extended, more accurate alignment of the femur, nail and guide may be achieved.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A method of treating a fracture of a distal portion of a femur comprising the steps of:

exposing a distal end of said femur;

extending an intramedullary nail into the medullary space of the femur from said distal end of said femur, said intramedullary nail comprising an elongate member having a proximal end and a distal end, said proximal end located near said distal end of said femur when said intramedullary nail is positioned in said femur, said intramedullary nail spanning a fracture of said femur;

positioning at least one blade member in a portion of said distal end of said femur which is distal of said fracture of said femur, said at least one blade member positioned generally transverse to said intramedullary nail;

fixing said at least one blade member to said intramedullary nail to generally prevent movement of said at least one blade member with respect to said intramedullary nail; and fixing said distal end of said intramedullary nail with respect to said femur.

2. The method in accordance with claim 1 wherein said positioning step comprises extending said blade through a blade passage in said proximal end of said intramedullary nail.

3. The method in accordance with claim 2 wherein said blade passage extends generally transverse to said intramedullary nail along a portion thereof adjacent to said passage.

4. The method in accordance with claim 2 wherein said fixing step comprises extending a locking screw through a portion of said intramedullary nail into engagement with said blade.

5. The method in accordance with claim 4 wherein said intramedullary nail includes a proximal tip at said proximal end and a passage extending from said proximal tip through said intramedullary nail to said blade passage and wherein said locking screw is extended through said passage.

6. The method in accordance with claim 1 wherein said intramedullary nail has a blade passage extending there through and said step of fixing comprises positioning a portion of said blade having a surface thereon configured to engage said passage in a manner resisting rotation of said blade with respect to said passage within said passage.

7. The method in accordance with claim 1 including the step of fixing at least a portion of said blade with said portion of said femur distal of said fracture.

8. The method in accordance with claim 1 wherein said blade has at least one end defining at least two generally planar surfaces which intersect and said step of fixing at least a portion of said blade with said portion of said femur comprises locating said portion of said blade defining said intersection of said planar surfaces into engagement with said femur.

9. The method in accordance with claim 8 wherein said surfaces intersect at an acute angle.

10. The method in accordance with claim 8 wherein said surfaces intersect at an angle of approximately ninety degrees.

11. The method in accordance with claim 1 wherein said intramedullary nail includes a locking member accepting passage through said distal end thereof and including the step of extending a locking member into said femur and said locking member accepting passage.

12. The method in accordance with claim 11 wherein said locking member comprises a threaded member.

13. The method in accordance with claim 1 including the step of extending a first blade member through a passage in said intramedullary nail and extending a second blade member through a passage in said intramedullary nail, said first blade member being freely moveable in said passage and said second blade member fixing said first and second blade members to said intramedullary nail.

14. The method in accordance with claim 13 wherein said passage is generally oval in shape, said passage having a minimum dimension which is greater than a maximum dimension of said first or second blade member, whereby said first or second blade members positioned in said passage alone are permitted to rotate relative to said passage.

15. The method in accordance with claim 1 including the step of connecting a blade guide to said intramedullary nail, said blade guide having a guide passage there through, and including the step of forming a passage in said femur aligned with said guide passage.

16. The method in accordance with claim 15 including the step of affixing said blade guide to said proximal end of said intramedullary nail.

17. The method in accordance with claim 15 wherein said intramedullary nail has a blade passage there through for accepting said at least one blade member, and including the step of aligning said guide passage with said blade passage.

18. A method of treating a fracture of a distal portion of a femur comprising the steps of:
locating an intramedullary nail in the medullary space of the femur, said intramedullary nail having a proximal section positioned near a distal end of said femur, said proximal section having a blade passage extending there through, said intramedullary nail having a distal end, said distal end including at least one distal passage there through for receiving a locking member, said intramedullary nail spanning said fracture of said femur;
positioning at least one blade in a portion of said femur distal of said fracture thereof, said at least one blade extending through said blade passage in said intramedullary nail, said at least one blade having at least one portion including at least two outer surfaces meeting at an angle, said at least one portion engaging said portion of said femur distal of said fracture when positioned therein, whereby rotation of said portion of said femur distal of said fracture relative to said at least one blade is resisted;
fixing the position of said at least one blade relative to said intramedullary nail to prevent axial movement of said at least one blade relative to said intramedullary nail; and
engaging a locking member with said femur and said at least one distal passage through said distal end of said intramedullary nail.

19. The method in accordance with claim 18 wherein said blade passage extends through said intramedullary nail at generally perpendicular thereto.

20. The method in accordance with claim 18 wherein said engaging step comprises extending a threaded member from an exterior of said femur into said femur and said at least one distal passage.

21. The method in accordance with claim 18 wherein said fixing step comprises engaging a locking screw with said blade.

22. The method in accordance with claim 21 wherein said intramedullary nail includes a proximal tip at said proximal end and a threaded passage extending from said proximal tip to said blade passage, and wherein said step of engaging said locking screw comprises threading said locking screw into said threaded passage from said proximal tip of said intramedullary nail and into engagement with said blade.

23. The method in accordance with claim 18 wherein said blade has at least one surface thereon which is adapted to engage at least one surface of said blade passage to prevent relative rotation of said blade with respect to said blade passage.

24. The method in accordance with claim 18 including the step of extending a first blade and a second blade through said passage.

25. The method in accordance with claim 18 including the steps of exposing a distal end of said femur at a knee by flexing said knee and then locating said intramedullary nail, connecting a blade guide to said nail after location thereof in said femur, said blade guide having a passage there through, extending said knee, and then forming a passage in said femur aligned with said passage in said blade guide and said blade passage in said intramedullary nail.

26. An apparatus for treating a fracture of a distal portion of a femur comprising:
an intramedullary nail for extension into said femur from a distal end thereof, said intramedullary nail having a proximal end and a distal end, at least one passage through said distal end for accepting a locking member, a blade passage extending through said proximal end, said blade passage extending through said proximal end generally perpendicular thereto, a proximal tip located at said proximal end, a passage extending through said intramedullary nail from said proximal tip to said blade passage, said blade passage having at least one surface defining said blade passage; and at least one blade for positioning in a portion of said distal femur which is distal of a fracture of said femur, said at least one blade having at least one portion defining at least two generally planar surfaces which intersect and having at least one surface, which when placed in said blade passage interacts with said at least one surface defining said blade passage to resist rotation of said at least one blade with respect to said intramedullary nail.

27. The apparatus in accordance with claim 26 wherein said blade has a uniformly "I" cross-sectional shape along its length.

28. The apparatus in accordance with claim 26 including a first blade and a second blade, said first and second blades when engaging said passage alone permitted to rotate with respect thereto, and wherein when said first and second blades engage said passage at the same time, rotation of said first and second blades relative to said intramedullary nail is resisted.

29. The apparatus in accordance with claim 26 including a blade guide, said blade guide having a first portion adapted for connection to said proximal end of said intramedullary nail and a second portion including a passage there through for alignment with said blade passage in said intramedullary nail in forming a passage in said femur.

30. The apparatus in accordance with claim 26 wherein said first portion of said blade guide is a generally planar member.

31. The apparatus in accordance with claim 26 wherein said generally planar member has a first end with a passage therein for accepting a fastener for fastening said blade guide to said intramedullary nail.

32. The apparatus in accordance with claim 30 wherein said second portion of said blade guide extends from said first portion generally perpendicular thereto.

* * * * *